United States Patent [19]

Tsunekawa et al.

[11] Patent Number: 5,112,880
[45] Date of Patent: May 12, 1992

[54] LIGHT-CURABLE ORTHODONTIC BRACKET ADHESIVE

[75] Inventors: Masayoshi Tsunekawa, Camarillo; Raymond L. Ramirez, Oxnard, both of Calif.

[73] Assignees: Gingi-Pak, Camarillo, Calif.; Sankin Kogyo K.K. Industry Ltd., Tokyo, Japan

[21] Appl. No.: 491,002

[22] Filed: Mar. 9, 1990

[51] Int. Cl.$^5$ .............................. C08F 2.46; A61K 6/08
[52] U.S. Cl. ........................................ 522/81; 522/14; 523/116
[58] Field of Search .................... 522/81, 14; 523/116

[56] References Cited

U.S. PATENT DOCUMENTS

| | | |
|---|---|---|
| 3,949,477 | 4/1976 | Cohen et al. . |
| 4,134,929 | 1/1979 | Stoakley et al. . |
| 4,376,835 | 3/1983 | Schmitt et al. . |
| 4,435,160 | 3/1984 | Randklev . |
| 4,457,818 | 7/1984 | Denyer et al. . |
| 4,479,782 | 10/1984 | Orlowski et al. . |
| 4,527,979 | 7/1985 | McLean et al. . |
| 4,544,467 | 10/1985 | Bunker et al. . |
| 4,652,312 | 3/1987 | Grossman et al. . |
| 4,689,015 | 8/1987 | Denyer et al. . |
| 4,695,251 | 9/1987 | Randklev . |
| 4,762,863 | 8/1988 | Sasaki et al. ........................ 522/11 |
| 4,775,592 | 10/1988 | Akashane et al. . |
| 4,808,228 | 2/1989 | Randklev . |
| 4,814,362 | 3/1989 | Billington et al. . |

*Primary Examiner*—Marion E. McCamish
*Assistant Examiner*—Mark A. Chapman
*Attorney, Agent, or Firm*—Dianne E. Reed

[57] ABSTRACT

A light-curable orthodontic bracket adhesive composition is provided for bonding an orthodontic bracket to the surface of a human tooth. The composition contains a particulate filler material, an acrylate-based resin, and a photoinitiator composition effective to catalyze polymerization upon irradiation. A method of using the composition is also provided.

1 Claim, No Drawings

LIGHT-CURABLE ORTHODONTIC BRACKET ADHESIVE

TECHNICAL FIELD

The present invention relates generally to a method and composition for bonding ceramic or metallic orthodontic brackets to human teeth. More particularly, the invention relates to a novel light-curable, filled acrylate resin-based orthodontic bracket adhesive and a method for its use. In preferred embodiments the filler component of the adhesive contains ion-leachable fluoride. The adhesive offers the advantages of rapid bonding and high bond strength without need for priming.

BACKGROUND

In the practice of orthodontics, tension wires are frequently used to change the position of the teeth within the mouth. These wires are affixed to individual teeth by either enclosing the tooth in a band or by cementing a metal or ceramic bracket to the tooth using an adhesive, known in the art and referred to herein as an "orthodontic bracket adhesive". Brackets are currently more popular, as bands tend to promote dental caries in the region adjacent to the band, and are also somewhat inconvenient for the orthodontist, as they must be stocked in many different sizes.

A number of orthodontic bracket adhesives are known. For example, U.S. Pat. Nos. 4,435,160 and 4,695,251 to Randklev describe an orthodontic bracket adhesive composition which contains a non-toxic filler having an Mohs hardness of less than about 4.5, a polymerizable resin system and, optionally, an adjuvant such as an inhibitor, stabilizer, or pigment. The method of using the composition requires preliminary cleaning and etching of the tooth surface. U.S. Pat. No. 4,134,929 to Stoakley et al. describes an orthodontic bracket adhesive based on allyl 2-cyanoacrylate. Light-curable adhesive compositions are described in U.S. Pat. Nos. 4,457,818 and 4,689,015 to Denyer et al.; these compositions are stated to be useful, inter alia, as orthodontic bracket adhesives. The compositions contain a polymerizable composition of a polymerizable vinyl urethane prepolymer, ethylene (or triethylene) glycol dimethacrylate, and a catalyst system which includes compounds such as dimethylaminoethyl methacrylate and camphorquinone. U.S. Pat. No. 4,479,782 to Orlowski et al. also relates to a light-curable orthodontic bracket adhesive which contains an aromatic acrylate, an aliphatic acrylate, an $\alpha,\beta$-diketone, a tertiary amine, and, optionally, fillers, stabilizers, or the like.

The recent advances in light-curable adhesive compositions, exemplified by the Denyer et al. and Orlowski et al. patents, have given rise to a bonding procedure which is simpler and far more rapid than earlier systems involving chemical curing. Light-curable adhesives, for example, enable manipulation and tying of archwires immediately after application and curing. However, all of the bracket adhesive systems of which applicants are aware, including the relatively new light-curable systems, require application of primer prior to application of the adhesive. Application of primer requires an extra step in the bonding procedure, additional time, and a sensitive technique. A thin and uniform primer coat has to be carefully placed; otherwise, the brackets may drift and consistent high bond strength may not be achieved. Furthermore, after completion of curing, tooth surfaces adjacent the brackets may remain tacky due to unpolymerized monomer in the adhesive composition.

There is thus a need in the art for a light-curable orthodontic bracket adhesive which does not require pre-treatment of the tooth surface with primer, but which nevertheless provides good adhesion with a minimum of bracket drift.

OTHER RELATED REFERENCES

In addition to the patents cited in the preceding section, the following references are related to one or more aspects of the present invention.

U.S. Pat. No. 4,544,467 to Bunker et al. describes a light-curable dentin and enamel adhesive containing a phosphorus-containing polymerizable monomer, a sulfur-compound such as an alkali metal sulfur salt, a photoinitiator, and an optional peroxide compound to faciliate polymerization.

U.S. Pat. No. 3,949,477 to Cohen et al. relates to a method and apparatus for applying orthodontic brackets to the teeth.

The following patents relate to fluorine-releasing glasses in dental and orthodontic compositions: U.S. Pat. No. 4,808,228 to Randklev et al. (a glass ionomer cement powder containing carboxylic acids comminuted with a fluoroaluminosilicate glass); U.S. Pat. No. 4,775,592 to Akahane et al. (a fluoroaluminosilicate glass powder for use in a dental glass ionomer cement); U.S. Pat. No. 4,652,312 to Grossman et al. (a tetrasilicic fluormica glass-ceramic composition for use in preparation of dental restorations, i.e., plates, bridges, crowns, or the like); U.S. Pat. No. 4,376,835 to Schmitt et al. (a calcium aluminum fluorosilicate glass powder for use in a dental or bone cement); and U.S. Pat. No. 4,527,979 to McLean et al. (a powdered dental material containing a sintered mixture of calcium aluminum fluorosilicate glass and precious metals).

SUMMARY OF THE INVENTION

It is accordingly a primary object of the invention to address the aforementioned needs in the art, and to provide a method and composition which fulfill those needs.

It is another object of the invention to provide a novel light-curable orthodontic bracket adhesive composition which provides for consistent high bond strength and virtually no bracket drift during use.

It is also an object of the invention to provide a light-curable orthodontic bracket adhesive which achieves a rapid strong bond to both tooth and bracket without need for priming the tooth or bracket.

It is still another object of the invention to provide such an adhesive composition which enables easy removal of excess adhesive after application of the bracket, and does not require excessive clean-up of the teeth, i.e., because there will be no excess primer, either cured or uncured, after application of the bracket.

It is yet another object of the invention to provide a fluoride-releasing orthodontic bracket adhesive effective to substantially prevent decalcification of tooth surfaces adhered to and adjacent to the bracket during a prolonged period of use.

It is a further object of the invention to provide a method of using such a light-curable orthodontic bracket adhesive so as to adhere a metal or ceramic bracket to the surface of a tooth, without resort to a separate priming step to prepare the tooth surface.

Additional objects, advantages and novel features of the invention will be set forth in part in the description which follows, and in part will become apparent to those skilled in the art upon examination of the following, or may be learned by practice of the invention.

In one aspect, this invention provides a filled light-curable orthodontic bracket adhesive. This adhesive contains solid particulate filler, a resin which includes at least one methacrylate monomer, and a photoinitiator. In a preferred aspect the filler is a fluorosilicate glass or equivalent fluoride ion-leachable substance. In a yet more preferred aspect the filler, resin and photoinitiator are selected to give an adhesive composition, prior to cure, of:

a. particulate fluorosilicate filler, 25–80 wt. %;
b. resin containing one or more methacrylate monomers, 20–75 wt. %; and
c. a photoinitiator composition containing a tertiary amine and an $\alpha,\beta$-diketone (catalytic amount).

The adhesive does not require mixing of components prior to use, as cure is effected by irradiation rather than chemically, nor is pretreatment of the tooth surface with a primer necessary.

In another aspect of the invention, a method is provided for affixing an orthodontic bracket to an unprimed surface of a human tooth, the method comprising coating the bracket with the aforementioned filled bracket adhesive, applying the bracket to the surface of the tooth, and irradiating the area with light for a period of time effective to cure the adhesive. Usually, the tooth surface is given a brief phosphoric acid etch prior to application of the adhesive to ensure a top quality bond.

DETAILED DESCRIPTION OF THE INVENTION

Before the present method and compositions are disclosed and described, it is to be understood that this invention is not limited to the specifically identified components or modes of administration disclosed herein, as such components or modes of administration may, of course, vary. It is also to be understood that the terminology used herein is used for the purpose of describing particular embodiments only and is not intended to be limiting.

It must be noted that as used in this specification and the appended claims, the singular forms "a", "an" and "the" include plural reference unless the context clearly dictates otherwise. Thus, for example, reference to "a filler" or to "a photoinitiator" includes mixtures of such compounds as well as their functional equivalents, while reference to the "method of use" will include variants thereon which are known to those skilled in the art or which will become known to those skilled in the art upon reading this disclosure.

As noted above, the orthodontic bracket adhesive of the invention is a light-curable, preferably fluoride-releasing composition which does not require mixing of separate components or application of primer prior to use, provides for quick cure, and displays high bond strength with both metallic and ceramic brackets.

The bracket adhesive preferably contains on the order of 25 wt. % to 80 wt. %, more preferably 50 wt. % material. The filler material may be selected from or based on a number of organic and inorganic adhesive filler materials known in the art, e.g., those described in U.S. Pat. Nos. 4,435,160 and 4,479,782, cited above. The filler must be non-toxic, insoluble in saliva, and of a nature such that it imparts a workable viscosity to the adhesive composition, i.e., enabling molding and manipulation during application. Suitable fillers are typically oxidic refractory inorganic materials which are clear or white in color. Representative fillers include polymethyl methacrylate, polyethyl methacrylate, quartz powders, silica gel, aluminum silicate, colloidal silica, glass beads, aluminum oxide, titanium dioxide, zirconia, and silicate or phosphate glasses. In preferred embodiments of the present invention, the filler should contain leachable fluoride so that it releases fluoride over the prolonged period of use, thereby substantially preventing decalcification of the tooth area adhered to and adjacent to the bracket. Particularly preferred fillers for use herein are the fluoride-releasing silicates, and a particularly preferred filler material for use herein is an aluminofluorosilicate glass such as strontium aluminofluorosilicate. Aluminofluorosilicate glass fillers are available commercially and can be prepared by art known methods as described, for example, in U.S. Pat. No. 4,775,592, the disclosure of which is incorporated by reference herein. See also U.S. Pat. Nos. 3,814,717, 4,360,605, and 4,376,835 for other descriptions of fluoride-containing glasses which can be used herein to advantage. If desired, the filler powder can be pretreated with a fluoro complex salt as is further detailed in the incorporated '592 patent.

It is preferred that the filler material be in the form of relatively small particles, i.e., having an average particle size less than about 50 microns in diameter, preferably less than about 25 microns in diameter, more preferably in the range of about 0.4 to 3 microns in diameter, and most preferably in the range of 0.4 to 1 micron in diameter. The smaller particle size, it has been found by the inventors herein, gives rise not only to better adhesion, but also to a higher rate of fluoride release, i.e., due to the greater surface area of the smaller particles. The smaller particle size also appears to minimize bracket drift.

The bracket adhesive also contains a light-curable, acrylate-based resin. In the preferred embodiment, the resin represents about 20 to 75 wt. %, more preferably 20 wt. % to 50 wt. %, most preferably about 20 wt. % to 40 wt. % of the adhesive composition. The polymerizable resin contains one or more photopolymerizable monomers selected from the group consisting of 2,2-bis p-(2'-hydroxy-3'-methacryloxypropoxy)-phenylene-propane (Bis-GMA), bis-phenol-A dimethacrylate, 2,2'-bis-(4'-methacryloxyethoxyphenyl)propane, methyl methacrylate, ethyl methacrylate, propyl methacrylate, hydroxyethyl methacrylate, hydroxypropyl methacrylate, diethyleneglycol dimethacrylate, triethylene glycol dimethacrylate, trimethylolpropane trimethacrylate, tetramethylene glycol dimethacrylate, pentaerythritol dimethacrylate, pentaerythritol trimethacrylate, dipentaerythritol dimethacrylate, glycerin trimethacrylate, ethylene glycol dimethacrylate, butanediol dimethacrylate, trimethylol propane trimethacrylate, tetramethylolmethane tetramethacrylate, and urethane methacrylates, i.e., virtually any type of methacrylate that is usable in dental and orthodontic applications and compositions. An example of an optimal formulation is one that contains, relative to the total adhesive composition, approximately 5 wt. % to 25 wt. %, optimally 10 wt. % to 20 wt. %, 2,2-bis p-(2'-hydroxy-3'-methacryloxypropoxy)-phenylene-propane (Bis-GMA); approximately 5 wt. % to 10 wt. % triethyleneglycol dimethacrylate; and approximately 2 wt. % to 3 wt. % 2-hydroxyethyl methacrylate Other components which may be used in addition to or in place of the aforementioned compounds will be readily ascertained by those skilled in the art and are described, for example, in U.S. Pat. Nos. 3,625,916, 3,629,187, 3,745,653, 3,955,282, 4,010,545 and 4,063,360, the disclosures of which are expressly incorporated by reference herein.

The bracket adhesive also contains an amount of a photoinitiator composition effective to catalyze polymerization upon irradiation. Generally, this effective amount will be in the range of approximately 2.4 wt. % to 11 wt. % relative to the total weight of polymerizable monomers. The photoinitiator composition acts as a source of free radicals when the bracket adhesive of the composition is irradiated. The photoinitiator compositions of the invention contain a tertiary amine reducing agent and an $\alpha,\beta$-diketone. A wide variety of tertiary amines may be used; however, preferred amines for use herein are selected from the group consisting of N,N-dimethylamino-p-toluidine, butyl diethanolamine, dimethylaminoethyl methacrylate, morpholinoethyl methacrylate, 2-methacryloxyethyl (p-N,N-dimethyl-)aminobenzoate, and dimethylamino benzoic acid or its esters. Similarly, a number of $\alpha,\beta$-diketones may be used. However, preferred $\alpha,\beta$-diketones for use herein are selected from the group consisting of camphorquinone, benzil, biacetyl, 9,10-phenanthrenequinone and naphthoquinone. Most preferred for incorporation into the present compositions is camphorquinone. Optimally, the present about 1.0 wt. % tertiary amine and 0.4 wt. % to about 1.0 wt. % $\alpha,\beta$-diketone relative to the resin.

The compositions of the invention may optionally include adjuvants such as inhibitors, stabilizers, pigments, or the like, as known in the art and as present in a number of the bracket adhesive compositions currently on the market.

The filled adhesive composition of this invention is prepared by simply mixing the various components with one another. The various resin materials are liquid and thus provide a suitable vehicle for the adhesive.

In use, the tooth to which the adhesive is to be applied is typically cleaned with conventional dental prophylactic paste, followed by etching the tooth surface with phosphoric acid, typically 35 wt. % to 45 wt. % phosphoric or orthophosphoric acid, for 15–90, optimally about 60 seconds. This etching procedure gives rise to a uniform surface for adhesion. The surface is then rinsed and air-dried.

The bracket adhesive is then applied to the bracket with a brush or a blade in such a way as to provide a uniform layer of adhesive. The adhesive of the invention, as established in the example, is useful with either ceramic or metal brackets. Generally, the layer of adhesive on the bracket will be in the range of about 50 to 200 microns. The bracket is then aligned and temporarily fixed, directly on the tooth surface, without the complication and delay of first applying a primer coat. Excess adhesive is removed and the adhesive is then photocured.

Photocuring is carried out using a sufficient intensity and duration of visible light exposure to harden the adhesive. Generally 5 to 50 seconds and more typically 10 to 30 seconds of light exposure using a conventional dental adhesive photocuring lamp at 300–500 nm wavelength, usually about 400 nm, gives a good bond.

In a typical case, when a metal bracket is used, the tooth and bracket are irradiated at about a 45° angle from each side of the bracket, i.e., from the gingival and occlusal sides of the tooth, for 10–20 seconds on each side. The light so presented is thus transmitted through the tooth to the area "behind" or "underneath" the bracket so to as to give a strong bond throughout the bonding region. Ceramic brackets, which are transparent to visible light, can be cured from above, i.e., at an approximately 90° angle to the bond interface. As soon as the light cure is complete, orthodontic wires can be filled and tied.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE

A bracket adhesive formulation of the invention was prepared by mixing the following:

Filler:
  Particulate (less than 1 micron i.d.) strontium aluminofluorosilicate, 75 wt. % (Nikon);

Resin:
  2,2-bis p-(2′-hydroxy-3′-methacryloxypropoxy)phenylene-propane ("Bis-GMA"), 15 wt. % (Freeman Chemical Corp., Port Washington, Wis.);
  Triethyleneglycol dimethacrylate, 7.5 wt. %, (Sartomer Co., Westchester, Pa.);
  2-Hydroxyethyl methacrylate, 2.5 wt. % (Rohmtech, Inc., Malden, Mass.)

Photoinitiator Composition:
  Methacryloxyethyl (p-N,N-dimethyl)amino benzoate, 4.0 wt. % relative to the resin (Sankin Co.); and
  d,l-Camphorquinone, 0.8 wt. % relative to the resin (Eastman Kodak, (Rochester, N.Y.).

The above adhesive was compared with the following commercially available formulations: Transbond TM (Unitek Corp./3M; batch no. 910 PCA); Achieve No-Mix TM ("A"-Company, Inc.; paste, batch no. 8E602; primer, batch no. 8L603; etchant, batch no. 7E901); and Quasar TM Debonding Adhesive (Rocky Mountain Orthodontics USA; batch no. 71202). Immediate bond strength following bonding and curing was evaluated with regard to both metal ("A" Company Metal Mesh U1 STD 0.018) and ceramic (Starfire TM U1 STD 0.018) brackets.

Extracted bovine teeth which had been stored in ethanol at room temperature were cut into pieces of approximately 1 cm$^2$ and embedded with a fast-cure acrylic resin (Sample-Kwick TM, Buehler, Ill.) in a cylindrical plastic mold (h=30 mm, d=20 mm). Prior to the preparation of the test specimen, the exposed enamel surfaces were ground wet with 800 grit silicon carbide paper on a polishing machine. The embedded tooth was then washed in running fluoride-free water and dried with an oil-free air syringe. The etching agents associated with the adhesives of each manufacturer were used in accordance with each manufacturer's instructions.

First, prior to applying the above formulation of the invention, the enamel surfaces were treated with 40% phosphoric acid for 60 seconds, then rinsed with running water for 10 seconds and dried with oil-free compressed air. The adhesive composition was then spread onto the bracket base with a spatula to ensure uniform coverage. Immediately after application of adhesive, the bracket was lightly placed onto the enamel surface and pressed firmly. Excess adhesive paste extruded around the bracket base was carefully removed. The adhesive layer was then irradiated with visible light (using an Optilux 400 TM, Demetron Research Corp.) for ten seconds. Ceramic brackets were cured at an angle of about 90 degrees to the bond interface at a distance of 5 mm. The bond adhesive under metal brackets was cured at a 45 degree angle for 15 seconds from the occlusal and another 15 seconds from the gingival edge. A total of 30 seconds curing time was required for the metal brackets.

Quasar TM Debonding Adhesive consists of a liquid monomer, adhesive powder and a catalyst. After mixing four drops of liquid monomer with one drop of catalyst a brush was dipped into the liquid-catalyst mixture and then into the adhesive powder to make a small bead. The bead was then spread evenly onto the bracket base. The bead-coated bracket was lightly pressed onto the etched enamel. After 8 minutes of curing, excess resin was carefully removed by using a razor blade. Shear bond strength was measured at the designated time.

Results are summarized in Tables 1 and 2.

TABLE 1

Shear Bond Strength of Orthodontic Adhesive (Metal Mesh U1 STD .018) in Kg: n = 10

| Adhesive Curing system | The Present Invention light/30 sec. | Transbond light/30 sec. | Achieve No-mix chem/60 sec. | Quasar Debonding chem/8 min. |
|---|---|---|---|---|
| Immediate | 11.25(2.40) | 10.35(1.71) | 3.96(0.85) | 8.23(0.75) |
| 5 min. | — | — | 8.67(1.76) | — |
| 1 hr. | 14.70(4.55) | 11.37(1.27) | 10.96(3.28) | 14.69(1.76) |
| 24 hr. | 19.18(1.29) | 15.34(2.34) | 15.48(2.19) | 19.37(2.77)**4 |

**4: Four out of ten specimens showed cohesive failures of tooth from potted resin.

TABLE 2

Shear Bond Strength of Orthodontic Adhesive (STARFIRE TM U1 STD .018) in Kg: n = 10

| Adhesive Curing system | The Present Invention light/10 sec. | Transbond light/10 sec. | Achieve No-mix chem/60 sec. | Quasar Debonding chem/8 min. |
|---|---|---|---|---|
| Immediate | 16.70(3.71)*4 | 17.01(3.38)*5 | 5.40(0.75) | 2.75(0.65) |
| 5 min. | — | — | 14.71(3.46) | — |
| 1 hr. | 17.94(3.24)*6 | 17.07(3.22)*5 | 14.01(3.23) | 9.69(2.28) |
| 24 hr. | 19.99(3.07)*7 | 19.05(2.01)*6 | 16.46(4.11)*3 | 15.30(4.65)*4 |

*#: Described numbers of specimen showed cohesive failures of STARFIRE bracket.

Bond strength was measured by an Instron universal testing machine (Model 1011; cross-head speed of 1 mm/min) at 60±10 seconds after the end of light curing. Ten specimens were tested for each time variable. Shear bond strengths at one hour and 24 hours were also evaluated. All specimens were immersed in 37° C. water until testing.

Transbond TM adhesive primer was brushed onto the etched enamel surface. A thin uniform coating was made by using a stream of oil-free compressed air. Transbond TM adhesive paste was syringed onto the bracket base, spread evenly and then placed onto the primed tooth surface. Firmly pressing the bracket, excess adhesive around the bracket base was carefully removed. Adhesive was then light cured in the same manner as with the above formulation of the invention.

Achieve No-Mix TM primer was applied to the bracket base and the etched enamel with a brush to make a thin uniform coating of primer. Achieve No-Mix TM adhesive paste was evenly spread on the primed bracket base with a plastic spatula. The adhesive paste-coated bracket was positioned onto the primed tooth surface and seated firmly. After 60 seconds, excess adhesive was carefully removed. Following the manufacturer's recommendations, a five-minute waiting period was required before the initial shear bond strength could be measured.

The formulation of the invention showed good immediate adhesion without the use of a primer. In comparison, under the same conditions, Transbond TM displayed a similar bond strength but required the use of a primer. Achieve No-Mix TM (chemical cure) showed poor immediate adhesion, but following the five-minute recommendation for the tying of archwires, showed an improved bond strength. Still, these values are significantly lower than the immediate bond strength of the light-cured adhesives. Achieve No-Mix TM requires a primer on the bracket as well as on the tooth surface, with the adhesive paste placed between them. In the case of Quasar TM Debonding Adhesive (chemical cure), following its recommended eight-minute waiting period, displayed a bond strength approximately equal to that of Achieve No-Mix TM after 5 minutes.

In sum, the data for immediate bond strength suggests that the light-cured adhesive formulation of the invention compared favorably with that of Transbond TM and was higher than that of the chemically cured adhesives for both metal and ceramic brackets. The present formulation, because no primer is required, is simpler to use and less-time consuming than formulations of the prior art. Furthermore, the present composition did not give rise to any bracket drift during placement, prior to curing, nor was there any problem arising from the presence of uncured monomer.

A summary of the benefits and deficiencies of the various orthodontic adhesive systems studied is presented in Table 3.

TABLE 3

Comparative procedures of orthodontic adhesive systems

| | Present Invention | Transbond TM | Achieve No Mix TM | Quasar Debonding Agent |
|---|---|---|---|---|
| Primer application | Not required | Required 1. Tooth surface with brush | Required Tooth and bracket surfaces with | Not required |

TABLE 3-continued

| | Comparative procedures of orthodontic adhesive systems | | | |
|---|---|---|---|---|
| | Present Invention | Transbond TM | Achieve No Mix TM | Quasar Debonding Agent |
| | | 2. Thin primer coating with air brush | | |
| Adhesive paste mixing | 1 paste | 1 paste | 1 paste | Powder/liquid/catalyst |
| Setting time under metal bracket | Light cure 30 sec. | Light cure 30 sec. | Chem. cure 60 sec. | Chem. cure |
| Setting time under ceramic bracket | Light cure 10 sec. | Light cure 10 sec. | Chem. cure 60 sec. | Chem. cure |
| Waiting time before placement of archwire | Not required immediate | Not required immediate | Required 5 min. | Required 7–8 min. |
| Bracket drift | Not a problem | Bracket may drift if primer coating is not thin enough | Primer not air-thinned; drifting a problem | Powder liquid ratio may affect drift |
| Removal of excess resin | Easy | Easy | Difficult if not removed within the first few min. | Fairly easy because curing takes longer |
| Clean-up of teeth after placement | Not required | Required uncured primer surrounding brackets | Required uncured primer surrounding brackets | Not required |

We claim:

1. A light-curable, orthodontic bracket adhesive composition comprising:
   (a) from approximately 60 wt. % to 80 wt. % particulate strontium aluminofluorosilicate filler having an average particle size in the range of about 0.4 to 1 micron;
   (b) from approximately 20 wt. % to 40 wt. % of a light-curable resin containing, relative to the total adhesive composition, approximately 5 wt. % to 25 wt. % 2,2-bis p-(2'-hydroxy-3'-methacryloxypropoxy)-phenylene-propane (Bis-GMA), approximately 5 wt. % to 10 wt. % triethyleneglycol dimethacrylate, and approximately 2 wt. % to 3 wt. % 2-hydroxyethyl methacrylate; and
   (c) a catalytically effective amount of a photoinitiator composition comprising approximately 2 wt. % to 10 wt. % 2-methacryloxyethyl (p-N,N-dimethyl) aminobenzoate and approximately 0.4 wt. % to 110 wt. % camphorquinone, relative to said resin.

* * * * *